United States Patent [19]

Brown et al.

[11] Patent Number: 5,014,353
[45] Date of Patent: May 14, 1991

[54] FACE SHIELD

[75] Inventors: Tobias Brown, Oak Park; Burton L. Siegal, Skokie, both of Ill.

[73] Assignee: Sellstrom Manufacturing Company, Palatine, Ill.

[21] Appl. No.: 451,516

[22] Filed: Dec. 14, 1989

[51] Int. Cl.⁵ .................................................. A61F 9/00
[52] U.S. Cl. .................................................. 2/11; 2/7; 2/9
[58] Field of Search .............. 2/7, 8, 9, 11, 410, 2/424, 427, 2, 206; 446/27; D16/105; D29/8, 9, 17; 16/110 R, 124; 220/94 A

[56] References Cited

U.S. PATENT DOCUMENTS

D. 224,576  8/1972  Galarneau ............................... 2/11
   969,528  9/1910  Bisbrow ............................. 16/111 R
 1,370,121  3/1921  King .
 1,508,907  9/1924  Work .
 1,652,973 12/1927  Bowers .
 2,056,027  9/1936  Tracey .
 3,555,559  1/1971  Hundhausen .
 3,943,271  1/1976  Rhee ........................................ 2/9

OTHER PUBLICATIONS

Safety Carrier for Glass Acid Bottles N. G. Schaffer, Western Electric.

Primary Examiner—Allan N. Shoap
Assistant Examiner—Daniel G. DePumpo
Attorney, Agent, or Firm—Neuman, Williams, Anderson & Olson

[57] ABSTRACT

A face protecting device comprising a generally concave shield having an inwardly projecting peripheral border portion and provided with an observation opening therein, said shield being further provided with two spaced angularly disposed hand grips in the lower portion thereof.

4 Claims, 1 Drawing Sheet

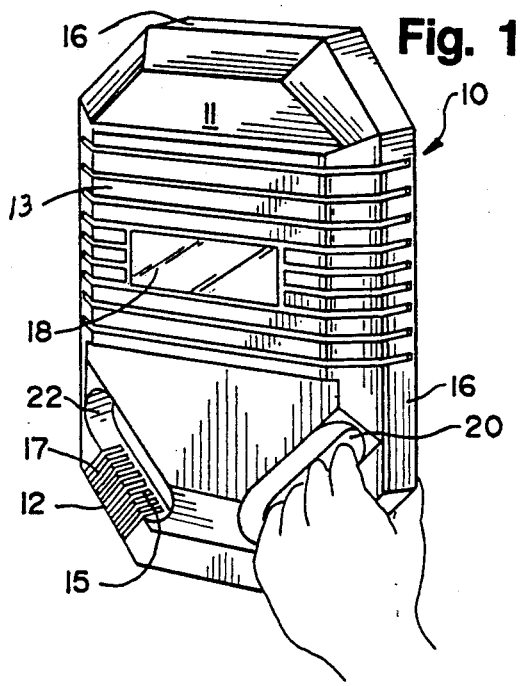
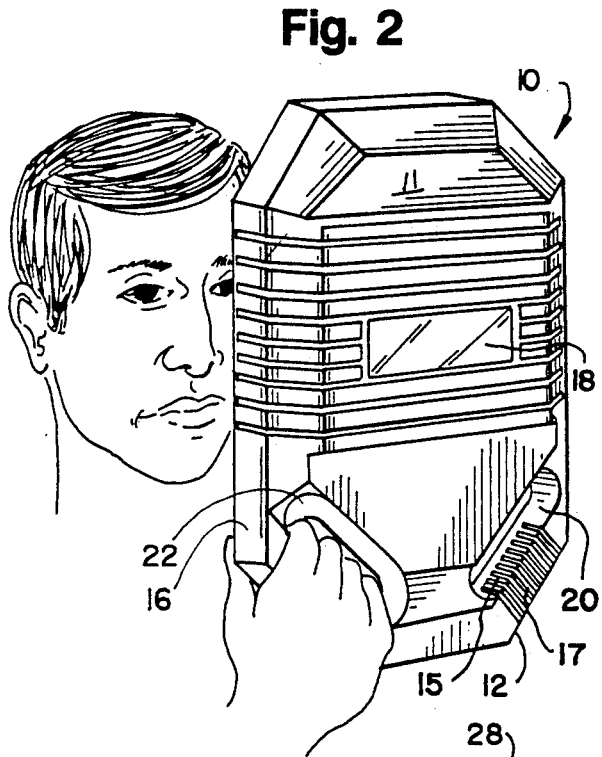
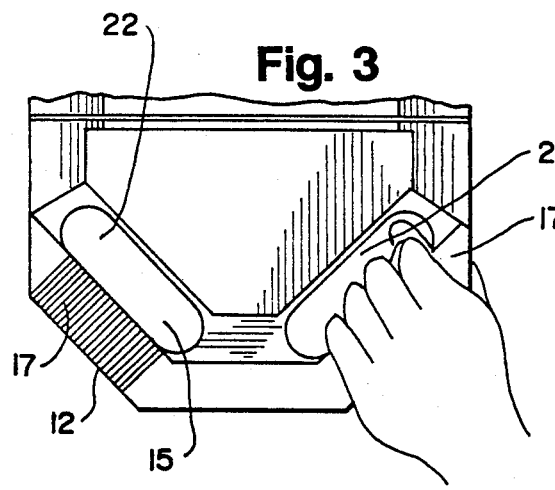
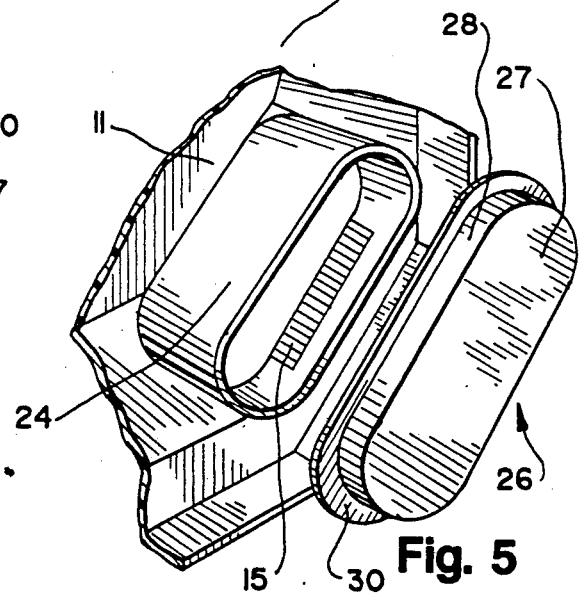
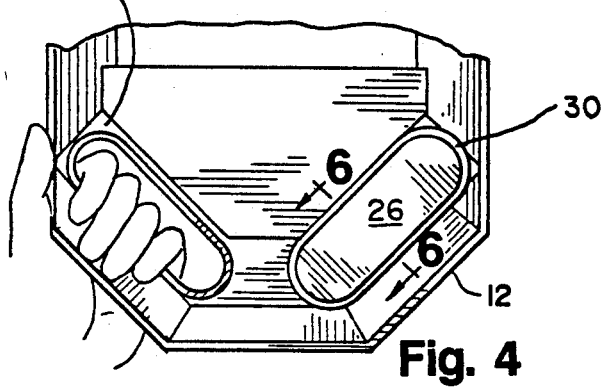
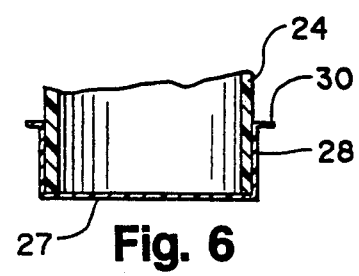

FACE SHIELD

This invention relates to a face protecting device of the type utilized by welders, metal workers and the like.

BACKGROUND

The present invention relates more particularly to hand-held shields of the type used by welders and others, such as supervisors and inspectors, for temporary observation as distinguished from the helmets or goggles which are normally worn by welders.

Temporary hand-held head shields are subjected to more or less rough usage and thus should be sturdy to withstand such usage but still be lightweight. Moreover, such shields should be compact and free of external appendages which are susceptible to breakage. Of course, hand held face shields should be convenient to grip and comfortably held by the user.

OBJECTS OF THE INVENTION

It is thus an object of this invention to provide a novel hand-held face protecting device.

It is a further object of this invention to provide a face protecting device which is sturdy, light in weight and which can be firmly gripped and comfortably held by the user.

It is a still further object of the invention to provide a hand-held face-protecting device provided with a hand-gripping means within the body of the device.

SUMMARY OF THE INVENTION

This invention provides a novel face shield which is light in weight, easy to manipulate and is constructed so that the user can readily grip and comfortably hold the shield in face protecting position.

The face protecting device comprises a generally concave shield having an inwardly projecting peripheral border portion to provide peripheral protection to the face. The shield is provided with an observation opening for receiving eye protecting screens. Two spaced, angularly disposed, ergonomically positioned hand grips are provided within the lower portion of the shield by means of which a user can grip and hold the shield in place using either the right or left hand.

DESCRIPTION OF THE DRAWINGS

FIG. 1 is a perspective view of the face-protecting device of this invention.

FIG. 2 illustrates the manner of use of the face-protecting device of the invention.

FIG. 3 is a front view of the lower portion of the face-protecting device showing a hand in one of the hand grip openings holding the device.

FIG. 4 is a rear view of the lower portion of the face-protecting device showing a hand in one hand grip opening holding the device.

FIG. 5 is a partial perspective rear view showing one of the hand grip openings and a cap for sealing the opening.

FIG. 6 is a view taken on line 6—6 of FIG. 4.

DESCRIPTION OF THE PREFERRED EMBODIMENTS

Referring to the drawings, the face-protecting shield 10 is generally concave and as shown has a frusto-octagonal body 11. The body 11 can take other shapes such as a more rounded or square configuration, however it is preferred that the lower portion 12 of the shield should have a generally pyramidal configuration for reasons which will be discussed. The shield is preferably formed of a lightweight non-flammable heat resisting opaque material which exhibits good impact resistance to withstand rough usage and penetration by flying sparks and molten metal such as encountered when welding. The body of the shield is preferably black in color in order to reduce light reflection. Suitable materials for forming the body include nylon, high density polyethylene, ABS and the like.

The body 11 can be readily formed as a unitary piece by appropriate shaping and cutting of a sheet of material or it can be formed by known molding procedures. In any event, the body is formed with a generally flat central face 13 and has a rearwardly extending border portion 16 around the periphery of the shield to provide peripheral protection to the eyes and face of the user.

The shield is provided with an observation opening 18 which is adapted to secure and hold an eye-protecting screen of a transparent material which protects the eyes of a user from infra-red, ultra-violet and part of the visible light emanating from the work area. As is customary, a relatively inexpensive, clear glass or plastic sheet can be placed over the screen.

Two angularly disposed hand grip openings 20 and 22 are provided in the lower portion of the shield. These openings are preferably disposed at an angle of about 45° which approximates the customary position of a hand when holding a telephone or the like. The angular positioning of the hand grip openings 20 and 22 is ergonomically correct and permits the hand of the user to be in a natural position without bending the wrist when holding the face shield in use. Prior art hand held face shields have external handles mounted to the central portion of the bottom of the shield which project downwardly therefrom in a line generally perpendicular to the line of sight. The position of such external handles for holding the face shield in place requires that the user's wrist be bent approximately 30°-40° from its natural position when the hand is placed in front of the face to grasp the perpendicularly extending handle. Holding the wrist in bent position for any length of time causes considerable physical stress to the forearm muscles with resultant fatigue and discomfort. Holding such a position for short durations, but repeatedly, produces the same fatigue and discomfort over time.

The hand grip openings 20 and 22 have a generally flattened elliptical shape with the walls 24 extending inwardly and are of a size to accommodate comfortably a user's gloved hand. The flat bottom surfaces 15 of the hand grip openings formed by a section of the rearwardly projecting border 16 provides a comfortable gripping surface by which the shield can be firmly held and manipulated. The relatively flat surfaces 15 and 17 in contact with the hand tend to provide for ease of holding the shield erect and resisting its gravitationally induced torque moment without additional gripping force by the user's hand.

A sealing cap 26 as illustrated in FIG. 5 made of any suitable non-inflammable, heat-resistant material can be used to close either hand grip opening 20 or 22, depending upon which opening is not being used at a particular time. The cap is of a size and shape to be preferably frictionally insertable over the edge of wall 24 of the hand grip openings from the rear of the shield. The cap can be attached by other suitable latching means to close either opening 20 or 22. The cap 26 is generally U-shaped with a flat bottom 27 with the upstanding wall portion 28 integrally joined thereto. A top peripheral flange 30 on the wall portion 28 assists in seating the cap and facilitates its removal from the hand grip openings The cap when inserted in one of the hand grip openings 20 or 22 further protects the neck of the wearer from radiation.

In the foregoing description of one preferred embodiment, openings 20 and 22 serve as the integral hand grips for the face-protecting device. In another embodiment, the integral hand grips are not complete openings but instead are provided with an integral back wall which serves to close the openings similarly to the flat bottom 27 of cap 26.

Those modifications and equivalents which fall within the spirit of the invention are to be considered a part thereof.

What is claimed is:

1. A face protecting device comprising a hand-held face shield having a generally concave body formed of a non-flammable material and with a projecting peripheral border thereon and provided with an observation window therein, said face shield being further provided with two spaced hand grips in the lower portion thereof angularly disposed to the vertical plane passing through the center of the face shield each handgrip defining an opening of a size and shape to allow the fingers of a hand to pass therethrough.

2. The device of claim 1 wherein said openings are disposed at an angle of about 45° from the vertical plane passing through the center of the face shield.

3. The device of claim 1 wherein said openings are generally elliptical in configuration with substantially flat hand-gripping surfaces.

4. A face protecting device comprising a hand-held face shield having a generally concave body formed of a non-flammable material and with a projecting peripheral border thereon and provided with an observation window therein, said face shield being further provided with two spaced hand grip openings in the lower portion thereof angularly disposed to the vertical plane passing through the center of the face shield and a cap member insertable on one or the other of said hand grip openings to close the opening.

* * * * *